(12) United States Patent
Nakagawa et al.

(10) Patent No.: US 8,182,761 B2
(45) Date of Patent: May 22, 2012

(54) TEST INSTRUMENT AND OPTICAL MEASUREMENT APPARATUS

(75) Inventors: Takashi Nakagawa, Kyoto (JP); Shinya Nakajima, Kyoto (JP); Tokuo Kasai, Kyoto (JP)

(73) Assignee: Arkray, Inc., Kyoto (JP)

( * ) Notice: Subject to any disclaimer, the term of this patent is extended or adjusted under 35 U.S.C. 154(b) by 263 days.

(21) Appl. No.: 12/517,776

(22) PCT Filed: Nov. 20, 2008

(86) PCT No.: PCT/JP2008/071138
§ 371 (c)(1),
(2), (4) Date: Jun. 4, 2009

(87) PCT Pub. No.: WO2010/058471
PCT Pub. Date: May 27, 2010

(65) Prior Publication Data
US 2011/0058994 A1  Mar. 10, 2011

(51) Int. Cl.
*G01N 21/75* (2006.01)
*G06Q 50/00* (2012.01)

(52) U.S. Cl. .......................................... 422/401; 705/3

(58) Field of Classification Search .................. 422/401; 705/3
See application file for complete search history.

(56) References Cited

U.S. PATENT DOCUMENTS

| | | | | |
|---|---|---|---|---|
| 4,264,560 A | * | 4/1981 | Natelson | 422/417 |
| 5,182,191 A | * | 1/1993 | Fan et al. | 435/7.9 |
| 5,710,008 A | * | 1/1998 | Jackowski | 435/7.4 |
| 6,550,683 B1 | * | 4/2003 | Augustine | 235/462.45 |
| 6,770,487 B2 | * | 8/2004 | Crosby | 436/518 |
| 7,278,579 B2 | * | 10/2007 | Loffredo et al. | 235/462.46 |
| 2005/0144044 A1 | * | 6/2005 | Godschall et al. | 705/3 |
| 2006/0180659 A1 | * | 8/2006 | Loffredo et al. | 235/380 |
| 2008/0019871 A1 | | 1/2008 | Sakamoto et al. | |
| 2011/0058993 A1 | * | 3/2011 | Nakagawa et al. | 422/401 |
| 2011/0058995 A1 | * | 3/2011 | Nakagawa et al. | 422/401 |
| 2011/0204139 A1 | * | 8/2011 | Nakajima | 235/380 |

FOREIGN PATENT DOCUMENTS

| | | |
|---|---|---|
| EP | 0366241 | 5/1990 |
| JP | 62-175667 | 8/1987 |
| JP | 2-210242 | 8/1990 |
| JP | 9-127120 | 5/1997 |
| JP | 2001-318101 | 11/2001 |
| JP | 2006-250787 | 9/2006 |
| JP | 2007-33293 | 2/2007 |
| WO | WO 2006/059694 | 6/2006 |

* cited by examiner

*Primary Examiner* — Lore Jarrett

(74) *Attorney, Agent, or Firm* — Fox Rothschild LLP

(57) ABSTRACT

It is an object to provide a test instrument and an optical measurement apparatus which enable easy matching of test results when tests by optical measurement are performed with respect to a large number of patients.

To the above end, a test instrument B is provided, which includes reagent retaining portions 8A, 8B, 8C retaining a reagent which reacts with a sample to produce a color reaction. The test instrument B includes a patient information entry section 64 as an example of patient identifying information region in which patient identifying information is to be written.

3 Claims, 11 Drawing Sheets

京都太郎 CH1  FluA: (+)1
              FluB: —

2007/10/31 09:02-09:17
ID:1234567890123457

京都花子 CH2  FluA: +
              FluB: **

2007/10/31 09:04-09:19
ID:1234567890123458

関西太郎 CH3  FluA: (+)1
              FluB: —

2007/10/31 09:06-09:21
ID:1234567890123459

関西花子 CH4  FluA: +
              FluB: **

2007/10/31 09:08-09:23
ID:1234567890123460

大和太郎 CH5  FluA: —
              FluB: —

2007/10/31 09:10-09:25
ID:1234567890123491

大和花子 CH6  FluA: +
              FluB: **

FIG.11

2007/10/31 09:02-09:17
ID:1234567890123457
京都花子　CH2　FluA: (+)1
　　　　　　　　　FluB: **

2007/10/31 09:00-09:15
ID:1234567890123456
京都太郎　CH1　FluA: (+)1
　　　　　　　　　FluB: —

2007/10/31 09:04-09:19
ID:1234567890123458
関西太郎　CH3　FluA: (+)1
　　　　　　　　　FluB: —

2007/10/31 09:06-09:21
ID:1234567890123459
関西花子　CH4　FluA: +
　　　　　　　　　FluB: **

2007/10/31 09:08-09:23
ID:1234567890123460
大和太郎　CH5　FluA: —
　　　　　　　　　FluB: —

2007/10/31 09:10-09:25
ID:1234567890123491
大和花子　CH6　FluA: +
　　　　　　　　　FluB: **

TEST INSTRUMENT AND OPTICAL MEASUREMENT APPARATUS

TECHNICAL FIELD

The present invention relates to a test instrument for optical measurement and an optical measurement apparatus for performing a test by reading the color development of a reagent of the test instrument.

BACKGROUND ART

Nowadays, various measurement apparatuses are used for POCT (Point of Care Testing) to be performed at hospitals, clinics, homes, etc., without relying on clinical examination specialists. Examples of such apparatuses include clinical examination apparatuses (see e.g. Patent Document 2) for performing optical reading with respect to an urine test strip (see e.g. Patent Document 1) once dipped in urine, or with respect to a biochemical test piece to which blood serum or blood plasma has been applied. Other examples are optical measurement apparatuses for performing measurement with respect to a cuvette (see e.g. Patent Document 3) with a liquid reagent contained.

FIG. 12 shows an example of conventional optical measurement apparatus (see e.g. Patent Document 4). To the illustrated optical measurement apparatus X, a test instrument Y for immunochromatography is mounted. The test instrument Y is a test piece in the form of a strip provided with a porous carrier 91. The porous carrier includes a plurality of reagent retaining portions 92 which retain a reagent (an immunologic substance, mainly antibodies) fixed to the portion. When a liquid sample such as blood or urine to be analyzed is applied to part of the test instrument Y, the sample infiltrates into the porous carrier 91. When the sample moving through the carrier reaches the reagent retaining portions 92, the sample reacts with the reagent. As a result, the reagent retaining portions 92 produces a color reaction in accordance with the concentration of a particular component contained in the sample.

FIG. 13 shows a typical urine test strip to be used by dipping in urine. The illustrated test strip 910 includes a base 911 in the form of a strip, and reagent retaining portions 912. Each reagent retaining portion 912 is provided on the base 911 and includes a carrier made of a porous matrix such as filter paper in which a reagent is fixed in an impregnated and dried state. When the reagent retaining portion 912 of the test strip 910 is dipped in a urine sample collected in e.g. a paper cup and pulled out, the urine sample infiltrated in the reagent retaining portion 912 through the carrier reacts with the reagent. After the lapse of a predetermined reaction period, the color development of the reagent retaining portion 912 is checked.

FIG. 14 shows an example of conventional optical measurement apparatus for the measurement of a biochemical test piece including a reagent retaining portion to which a sample of urine or blood serum/blood plasma extracted from blood is to be directly applied. The illustrated optical measurement apparatus 920 includes a table 922 on which biochemical test pieces 921 are to be mounted. Each test piece 921 includes a carrier made of at least one of a high polymer compound (e.g. paste represented by water-soluble polymer) and a porous film (such as knit fabric or nonwoven fabric). The reagent retaining portion is provided by fixing a reagent to at least one of the high polymer compound and the porous film in a dry state. To perform measurement using the optical measurement apparatus 920, a liquid sample such as blood or urine to be analyzed is directly applied to the reagent retaining portion of the test piece 921. The sample dissolves the high polymer compound forming the carrier or infiltrates into the porous film. Thus, the sample reacts with the reagent in the reagent retaining portion. After the lapse of a predetermined reaction period, the color development of the reagent retaining portion is checked.

FIG. 15 shows an example of test instrument of a cuvette type. The test instrument 930 shown in the figure includes a plurality of wells 931 and is made of e.g. a light-transmitting resin. Each of the wells 931 is used as a carrier, and a reagent retaining portion is provided by sealing a reagent in a liquid or solid state in the well 931. When a sample is put into a selected one of the wells 931 of the test instrument 930, the sample reacts with the reagent in the well 931. After a predetermined period of time, the well 931, which functions as the reagent retaining portion, develops color in accordance with the concentration of a particular component contained in the sample. Since the well 931 transmits light, the color development is easily checked from the outside.

Referring again to FIG. 12, the optical measurement apparatus X includes a light emitting means 93 and a light receiving means 94. When the test instrument Y is mounted to the optical measurement apparatus X, an instruction to start the test is given to the controller 95 by e.g. the user's operation. The controller 95 performs the light emitting operation for lighting the light emitting means 93 and the light receiving operation for receiving the light reflected by the porous carrier 91 including the reagent retaining portion 92 at the light receiving means 94. By the signal transmission from the light receiving means 94 to the controller 95, the image data of the reagent retaining portions 92 of the porous carrier 91 are stored in the controller 95. By analyzing the image data which corresponds to the color development of the reagent retaining portions 92, the presence or absence of a particular component in the sample is determined.

Though not illustrated, when the test instrument Y is an urine test strip similar to the test strip 910 shown in FIG. 13 or a biochemical test piece, the light reflection during or after the reaction of the sample with the reagent on the surface of the reagent retaining portion 912 (sometimes called a reagent pad) is measured by an exclusive device. When the test instrument Y is of a cuvette-type similar to the test instrument 930 shown in FIG. 15, the light reflection or light transmission after the reaction of the sample with the reagent in the well is measured through the light-transmitting surface of the well.

The test results obtained by the optical measurement are outputted by an output means 96 such as a printer. Based on the output results, the user can recognize the presence or absence of a particular component in the sample.

However, in the case of e.g. tests for influenza which are often performed by immunochromatography, tests for many patients are performed in e.g. a hospital in a short period of time. Thus, it is necessary to properly match each of the test results with the relevant patient. The same type of test piece Y is used for the same test item, and generally, the test result printed by the printer accompanies only the test time and serial number, for example. Thus, when the tests are performed with respect to many patients, the work to match each test result with the patient is troublesome. Moreover, when the tests of a plurality of items such as influenza and allergy are performed, the time required for the tests differs among the test pieces Y. In this case, to match the printed test result with the test item or the patient is more difficult.

Patent Document 1: PCT W02006/059694
Patent Document 2: JP-A-09-127120
Patent Document 3: JP-A-2001-318101
Patent Document 4: JP-A-2006-250787

DISCLOSURE OF THE INVENTION

Problems to be Solved by the Invention

The present invention has been proposed under the circumstances described above. It is, therefore, an object of the present invention to provide a test instrument and an optical measurement apparatus which enable easy matching of test results when tests by optical measurement are performed with respect to a large number of patients.

Means for Solving the Problems

According to a first aspect of the present invention, there is provided a test instrument comprising at least one reagent retaining portion retaining a reagent which reacts with a sample to produce a color reaction. The test instrument includes a patient identifying information region in which patient identifying information is to be entered.

In a preferred embodiment of the present invention, the test instrument further comprises a carrier to which a sample is to be applied, and the at least one reagent retaining portion comprises part of the carrier which retains the reagent.

In a preferred embodiment of the present invention, the test instrument is a test piece for immunochromatography. The carrier comprises a porous film. The reagent retaining portion is provided by fixing an immunologic substance to the porous film. The patient identifying information region is provided at part of the porous film.

In a preferred embodiment of the present invention, the test instrument is a test piece for immunochromatography. The carrier comprises a porous film. The reagent retaining portion is provided by fixing an immunologic substance to the porous film. The test instrument further comprises a case accommodating the carrier and including a measurement window exposing the reagent retaining portion. The patient identifying information region is provided at part of the case.

In a preferred embodiment of the present invention, the test instrument is a test strip to be dipped in a liquid. The carrier comprises a porous film. The reagent retaining portion is provided by fixing an immunologic substance in a dry state to the porous film. The test instrument further comprises a base to which the reagent retaining portion is bonded. The patient identifying information region is provided on the base.

In a preferred embodiment of the present invention, the test instrument is a test piece which is so designed that a sample is to be dropped onto the reagent retaining portion. The carrier comprises at least one of a high polymer compound and a porous film. The reagent retaining portion is provided by fixing the reagent in a dry state to at least one of the high polymer compound and the porous film. The test instrument further comprises a base to which the reagent retaining portion is bonded. The patient identifying information region is provided on the base.

In a preferred embodiment of the present invention, the test instrument is a light-transmitting cuvette including a plurality of compartments. The carrier comprises a light-transmitting compartment. The reagent retaining portion is provided by sealing the reagent in a liquid or solid state in the compartment. The test instrument further comprises a sealing member for hermetically sealing the compartment. The patient identifying information region is provided on the sealing member.

In a preferred embodiment of the present invention, the test instrument is a light-transmitting cuvette including a plurality of compartments. The carrier comprises a light-transmitting compartment. The reagent retaining portion is provided by sealing the reagent in a liquid or solid state in the compartment. The patient identifying information region is provided on a side surface of the light-transmitting compartment.

In a preferred embodiment of the present invention, the patient identifying information region is raised relative to the surrounding portion.

In a preferred embodiment of the present invention, the patient identifying information region has a surface which is rougher than the surface of the surrounding portion.

According to a second aspect of the present invention, there is provided an optical measurement apparatus to be used with at least one test instrument according to the first aspect of the present invention mounted to the apparatus. The optical measurement apparatus comprises a reader for reading color development of the reagent retaining portion, and a controller for performing drive control of the reader and test processing. The reader is capable of reading the patient identifying information region. The controller generates test result output data using the image data of the patient identifying information region obtained by the reading operation of the reader.

In a preferred embodiment of the present invention, the optical measurement apparatus further comprises a printer as output means. The printer performs printing based on the test result output data transmitted from the controller.

In a preferred embodiment of the present invention, the optical measurement apparatus further comprises an external connector as output means. The controller is capable of transmitting the test result output data through the external connector.

In a preferred embodiment of the present invention, the optical measurement apparatus is so designed that a plurality of said test instruments can be mounted.

Other features and advantages of the present invention will become more apparent from the detailed description given below with reference to the accompanying drawings.

BRIEF DESCRIPTION OF THE DRAWINGS

FIG. 9 is a plan view of the sheet showing the results of the test of FIG. 8.

FIG. 11 is a plan view of the sheet showing the results of the test of FIG. 10.

BEST MODE FOR CARRYING OUT THE INVENTION

Figure 1:
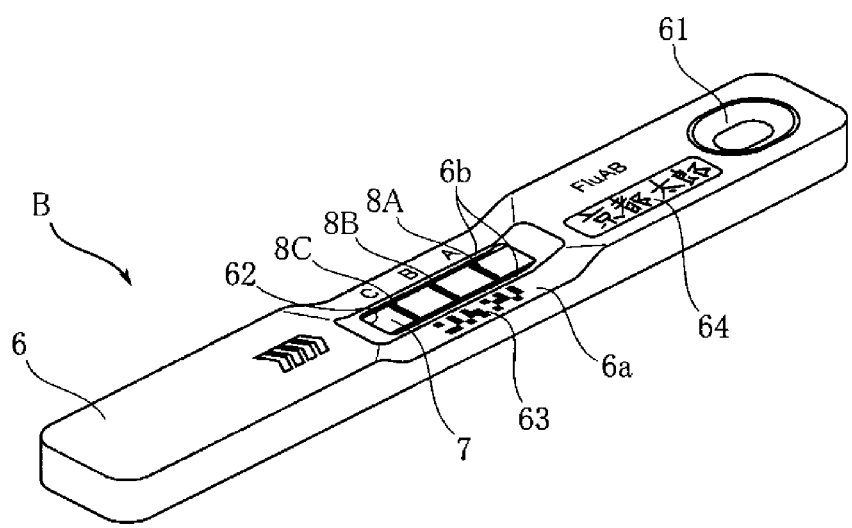
FIG. 1 is an overall perspective view showing an example of test instrument according to the present invention.

Preferred embodiments of the present invention will be described below with reference to the accompanying drawings.

FIGS. 1-5 show an example of test instrument according to the present invention. The test instrument B of this embodiment includes a case 6, a carrier 7 and reagent retaining portions 8A, 8B, 8C to which an immunologic substance such as an antibody is fixed. As will be described later, the test instrument is to be mounted to an optical measurement apparatus such as an apparatus for immunochromatography and used for the optical measurement by immunochromatography. Specifically, the test instrument B may be used for the tests for influenza.

The case 6 comprises a base 6B and a cover 6A elongated and made of e.g. a white resin and accommodates the carrier 7 made of a porous matrix. The case 6 includes an application portion 61, a measurement window 62, a test item code 63 and a patient information entry section 64 and is formed with a dented portion 6a and an inclined surface 6b.

The application portion 61 is a portion to which a sample is applied. The application portion comprises a through-hole formed in the cover 6A to expose an end of the carrier 7 and a crater-shaped portion surrounding the through-hole. The measurement window 62 comprises an elongated through-hole formed at the center of the cover GA and exposes the reagent retaining portions 8A, 8B, 8C formed at the carrier 7. The test item code 63, which may be a printed barcode (a two-dimensional code in the illustrated example), is provided for indicating the test item that can be tested by the test instrument B.

Figure 2:
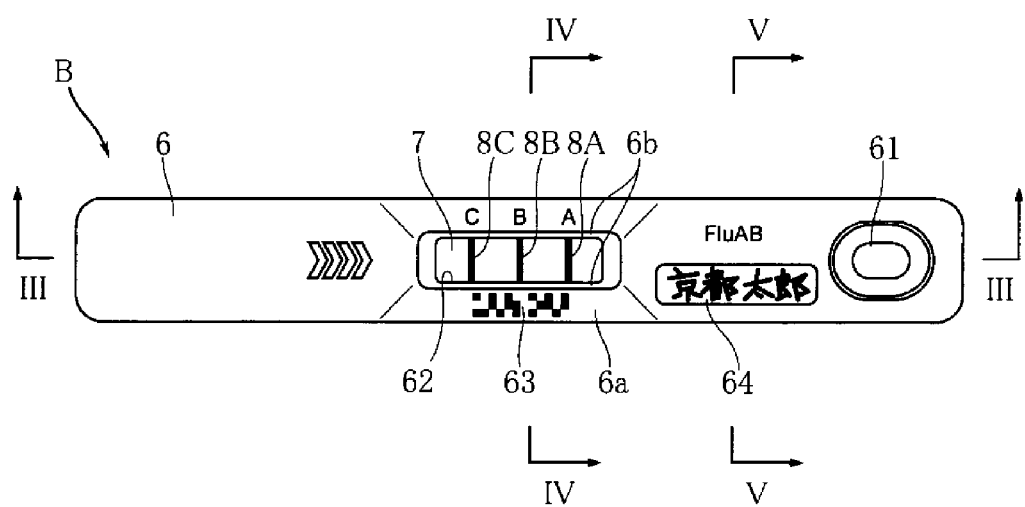
FIG. 2 is a plan view of the test instrument shown in FIG. 1.
Figure 4:
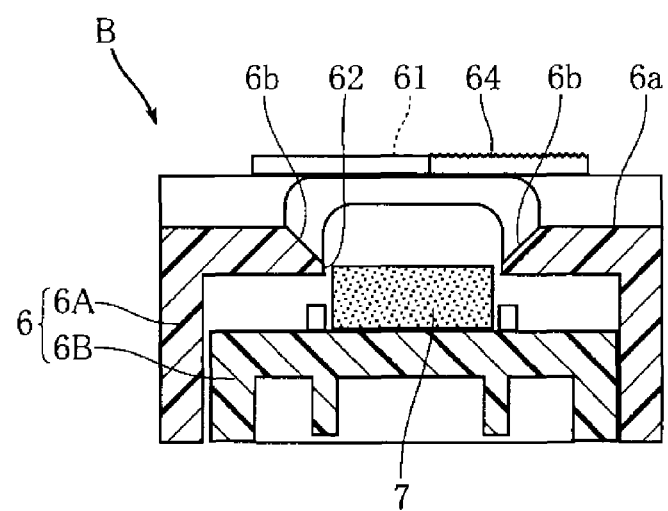
FIG. 4 is a sectional view taken along lines IV-IV in FIG. 2.
Figure 5:
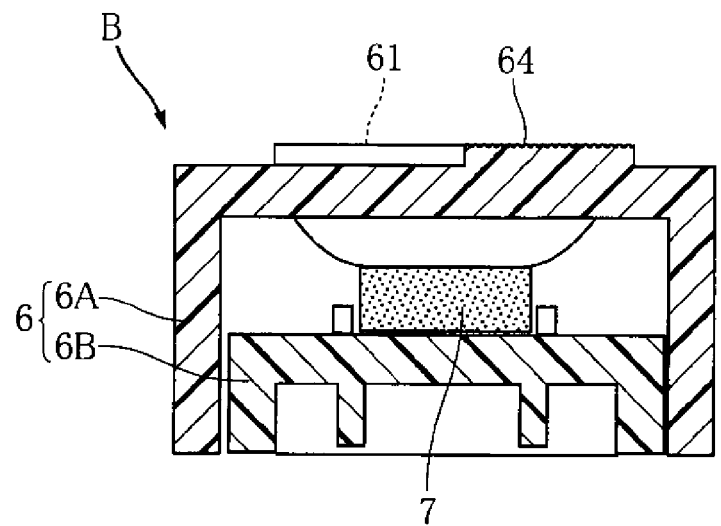
FIG. 5 is a sectional view taken along lines V-V in FIG. 2.

The patient information entry section 64 is a region in which information such as the name of the patient taking the test is to be manually written. The patient information entry section is an example of patient identifying information region in the present invention. As shown in FIGS. 2 and 4, the patient information entry section 64 in this embodiment is in the form of a rectangular platform raised relative to the surrounding portions. As shown in FIG. 5, the surface of the patient information entry section 64 is grained and rougher than the surfaces of other portions. In the patient information entry section of the illustrated example, the name of the patient who provided the sample for the test with the test instrument B is handwritten by the patient himself or herself or the user, i.e. a nurse or a clinical laboratory technologist for example, using a writing tool such as a felt-tip pen. Although it is assumed that the name of the patient is to be written in the patient information entry section 64, any other information such as the identification number of the patient in the organization to which the patient belongs to or the patient's nickname may be written as long as the given information can identify the patient.

Figure 3:
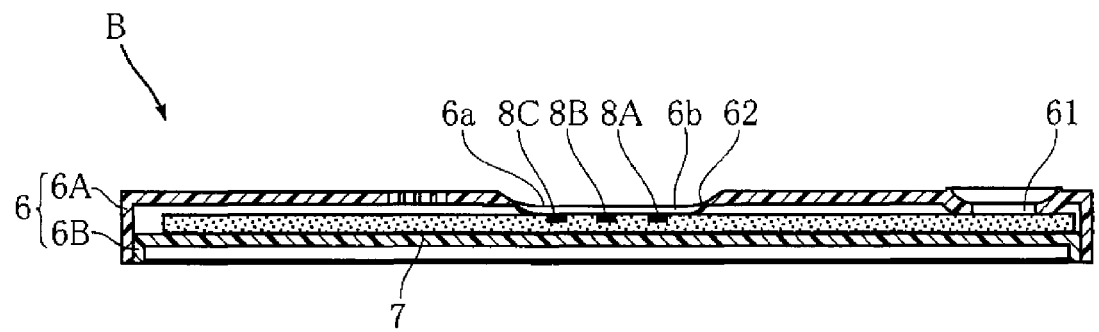
FIG. 3 is a sectional view taken along lines III-III in FIG. 2.

The measurement window 62 is provided at the dented portion 6a. As shown in FIG. 3, the dented portion 6a is closer to the carrier 7 than the portions sandwiching the dented portion 6a in the longitudinal direction of the case 6 are. In this embodiment, the test item code 63 is applied to the dented portion 6a to adjoin the measurement window 62 in the width direction of the case 6. The inclined surface 6b is connected to the measurement window 62 in the width direction of the case 6. In this embodiment, the inclined surface 6b is inclined 45 degrees with respect to the width direction of the case 6.

Though not illustrated, when the test instrument B is a urine test strip, the test instrument includes a base and reagent retaining portions 8A and 8B formed on the base. In this case, each of the reagent retaining portions 8A and 8B is structured as a reagent pad provided by impregnating and drying a reagent in a carrier. The reagent retaining portions are designed for the testing of a plurality of items such that the reagent retaining portion 8A is for testing glucose while the reagent retaining portion 8B is for testing protein, for example. A test item code 63 is printed on the support to show what kind of items the test instrument B measures.

Figure 15:
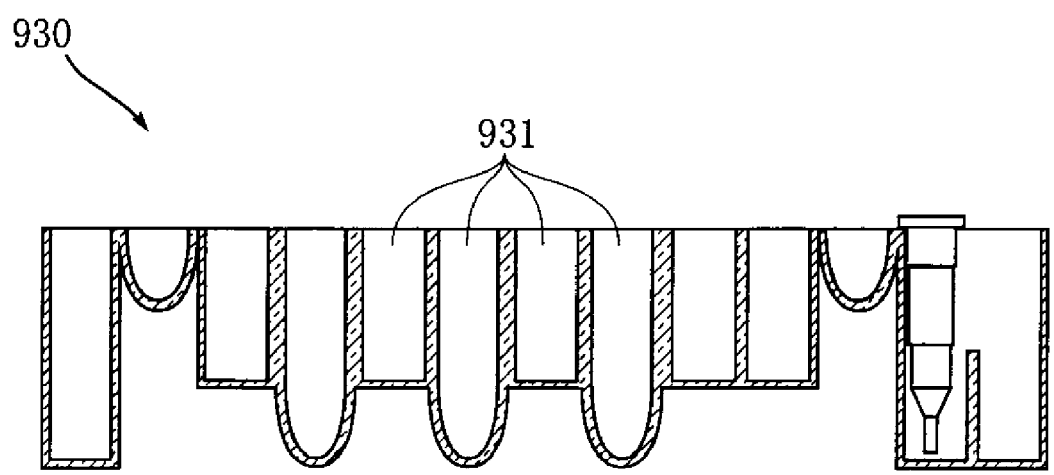
FIG. 15 is a sectional view showing an example of conventional test instrument of a cuvette type.

When the test instrument B is of a cuvette type, each of the compartments (hereinafter referred to as "well") in the cuvette corresponds to the carrier 7. By sealing a reagent in a liquid or solid state in the wells, the wells function as reagent retaining portions 8A and 8B. A test item code 63 may be printed on the surface of an aluminum laminate which hermetically seals the well to prevent the content from leaking out of the well. A patient information entry section 64, which is an example of patient identifying information region, may also be provided on the surface of the seal. Alternatively, the patient information entry section 64 may be provided on the side surface of a well which is not directly related to the optical measurement. For instance, the patient information entry section may be provided on the side surface of a well for holding a pipette tip (the well on the right end in FIG. 15) or a well for storing waste liquid after the use for the measurement.

In a test instrument B for immunochromatography, the carrier 7 is a porous member for causing the sample applied to the application portion 61 to spread over the reagent retaining portions 8A, 8B and 8C and may comprise a strip made of e.g. nitrocellulose. In a urine test strip, a biochemical test piece or a cuvette-type test instrument, the carrier 7 is a pad made of at least one of a porous film and a high molecular compound impregnated with a reagent or a well constituting the cuvette.

In this embodiment which employs immunochromatography as an example, the reagent retaining portions 8A, 8B, 8C are provided by fixing a reagent (immunologic substance such as an antibody) to part of the carrier 7. Specifically, the reagent retaining portions 8A and 8B are provided by fixing e.g. a reagent for determining positive or negative in tests for influenza. The reagent retaining portions 8A and 8B extend linearly in the width direction of the carrier 7 and are generally called a "test line". The number of reagent retaining portions 8A and 8B may be increased as desired depending on the target to be tested. Although these reagent retaining portions are generally called "test line", they may not be linear but may be in the form of a spot. In a urine test strip, the reagent retaining portion 8A is a reagent pad for testing a single item. Theoretically, therefore, when a urine test strip includes ten reagent retaining portions, the urine test strip is capable of testing ten items.

The reagent retaining portion 8C is utilized for determining whether or not the sample has properly passed through the reagent retaining portions 8A and 8B, which are the test lines, and is generally called a "control line". The reagent retaining portion 8C is provided by fixing e.g. a reagent which develops color due to the reaction with a sample and extends linearly in the width direction of the carrier 7. Unlike this, when the test instrument is an urine test strip or a cuvette-type test instrument, a reagent may not be put into the reagent retaining portion 8C so that the reagent retaining portion can be utilized as a control pad or a control well for optically canceling the influence of hemolysis or dark colored urine caused by taking a medicine, for example.

Figure 6:
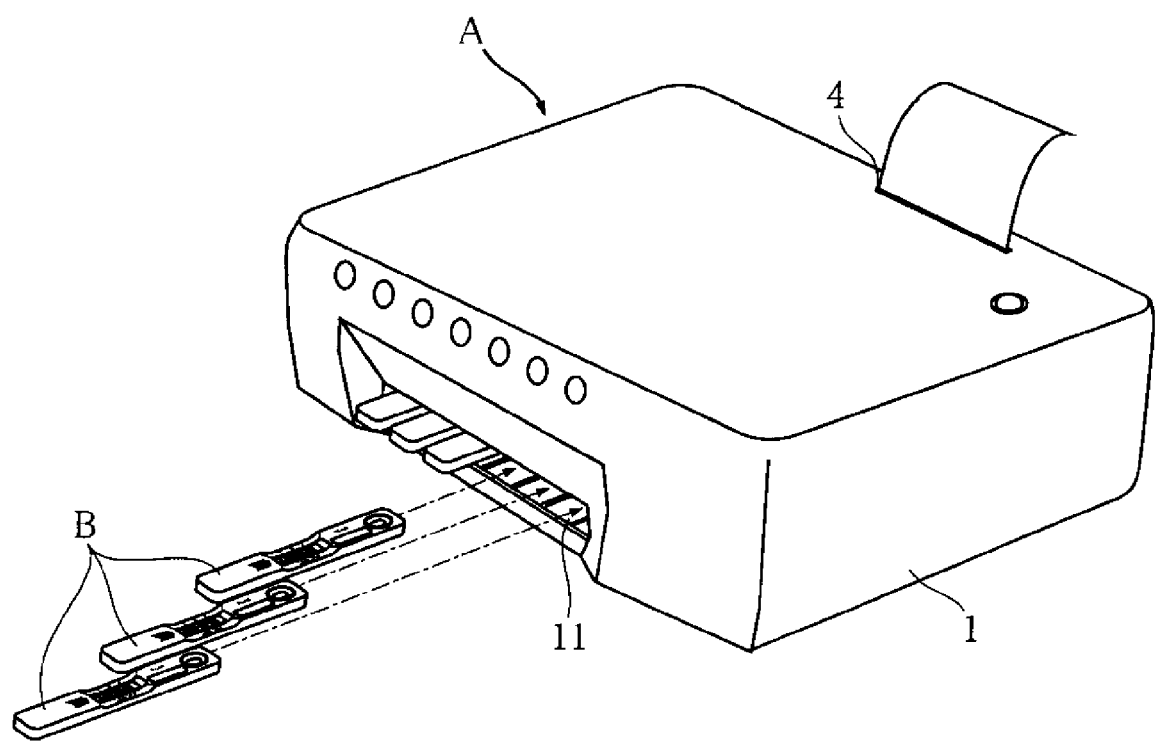
FIG. 6 is an overall perspective view showing an example of optical measurement apparatus according to the present invention.
Figure 7:
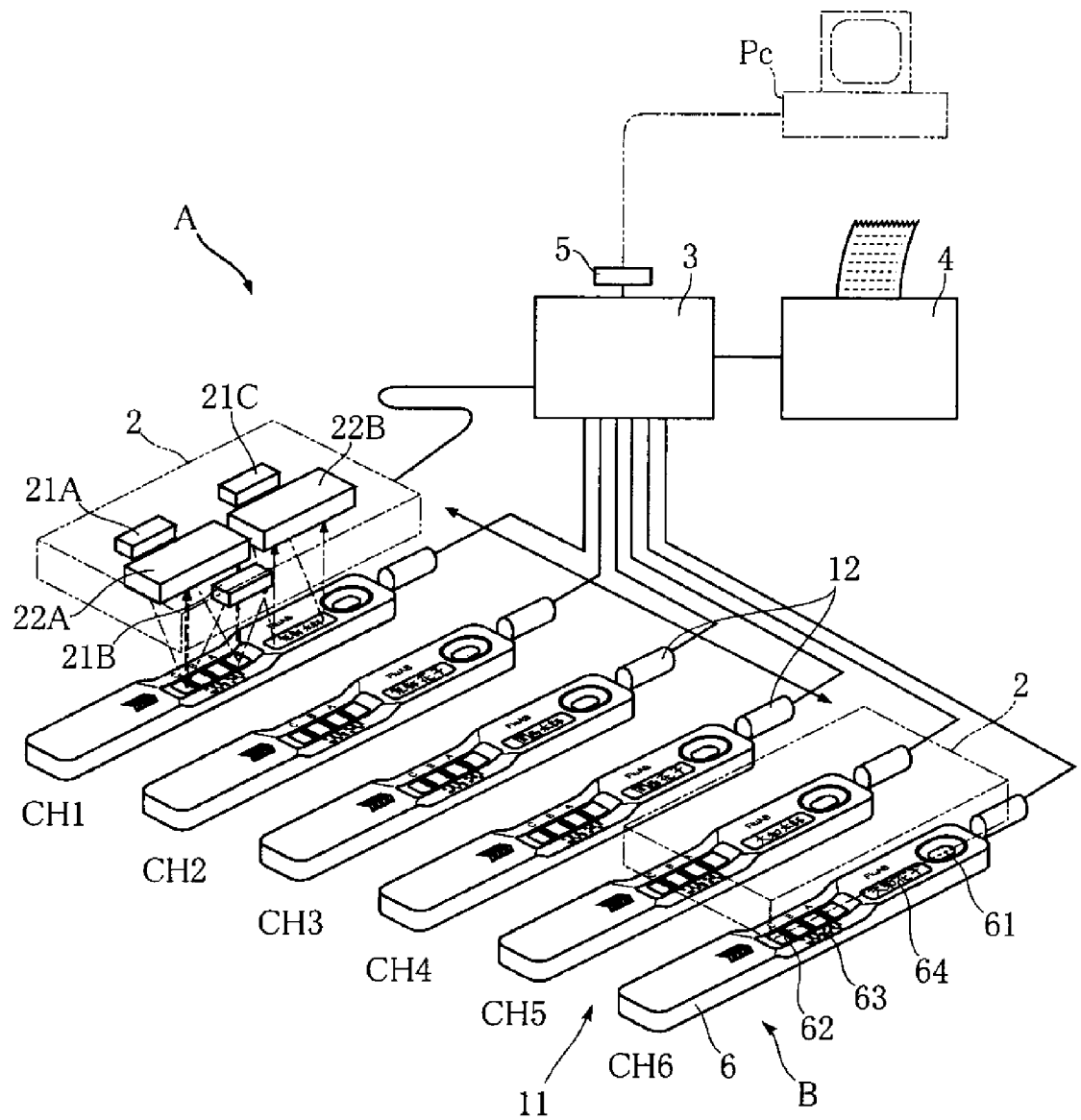
FIG. 7 is a system structure diagram of the optical measurement apparatus shown in FIG. 6.

FIGS. 6 and 7 show an example of optical measurement apparatus according to the present invention. The optical measurement apparatus A of this embodiment includes a case 1, a reader 2, a controller 3, a printer 4 and an external connector 5. The apparatus is designed to perform an immunochromatography test by checking the color development of the test instrument B mounted to the apparatus. In FIG. 7, the illustration of the case 1 is omitted for easier understanding.

As shown in FIG. 6, the case 1 of the optical measurement apparatus A, which may be made of e.g. a resin or a metal, accommodates the reader 2, the controller 3, the printer 4 and the external connector 5, which are the other structural elements of the optical measurement apparatus A. The case 1 includes a mount portion 11. A test instrument B to which a sample is applied is to be mounted to the mount portion 11. In this embodiment, the mount portion 11 is made up of six sections CH1-CH6 so that six test instruments B at the most can be mounted at a desired timing. A plurality of LED lamps are provided directly above the mount portion 11. When a test instrument B is mounted to the mount portion 11 at a position directly below one of the LED lamps, the LED lamp emits light of a predetermined color to indicate the mounting of the test instrument. When the test of the test instrument B is completed, the LED lamp emits light of a predetermined color to indicate the completion of the test. As shown in FIG. 7, six sensors 12 are provided at the mount portion 11. The sensors 12 are utilized for determining to which of the sections CH1-CH6 the test instrument B is mounted.

As shown in FIG. 7, the reader 2 includes light emitting modules 21A, 21B, 21C and light receiving sensor modules 22A, 22B. The light emitting modules 21A, 21B and the light receiving sensor module 22A are utilized for reading the reagent retaining portions 8A, 8B, 8C through the measurement window 62 of the test instrument B and reading the test item code 63. The light emitting module 21C and the light receiving sensor module 22B are utilized for reading the patient information entry section 64. In the reader 2, the light emitting modules 21A, 21B, 21C and the light receiving sensor modules 22A, 22B may be supported and driven collectively. Alternatively, for instance, the light emitting modules 21A, 21B and the light receiving sensor module 22A may be supported and driven separately from the light emitting module 21C and the light receiving sensor module 22B. Unlike this embodiment, all of the reagent retaining portions 8A, 8B, 8C, the test item code 63 and the patient information entry section 64 may be read by a single light receiving sensor module 22A. In this case, the light receiving sensor module 22A may be designed to have a relatively wide light receiving area.

The light emitting modules 21A and 21B incorporate e.g. LEDs and emit light of different wavelengths. Each of the light emitting modules 21A and 21B emits linear light extending in the longitudinal direction of the test instrument B. The light receiving sensor module 22A may include a plurality of photodiodes arranged in a row or an optical sensor such as an area sensor and generates an output corresponding to the luminance of the received light. The light receiving area of the light receiving sensor module 22A is in the form of a narrow strip extending in the longitudinal direction of the test instrument B. In this embodiment, when the reader 2 is positioned directly above a test instrument B, the light receiving sensor module 22A faces the measurement window 62 and the light emitting modules 21A and 21B emit light toward the measurement window 62 at an angle of about 45 degrees from the opposite sides of the light receiving sensor module 22A. By selectively irradiating the reagent retaining portions 8A, 8B, 8C with light of different wavelengths from the light emitting modules 21A and 21B, the reagent retaining portions can be read as image data of at least two kinds of color phases.

The light emitting module 21C incorporates e.g. an LED and emits light of a predetermined wavelength. Specifically, the light emitting module 21C emits linear light extending in the longitudinal direction of the test instrument B. The light receiving sensor module 22B may include a plurality of photodiodes arranged in a row or an optical sensor such as an area sensor and generates an output corresponding to the luminance of the received light. The light receiving area of the light receiving sensor module 22B is in the form of a narrow strip extending in the longitudinal direction of the test instrument B. In this embodiment, when the reader 2 is positioned directly above a test instrument B, the light receiving sensor module 22B faces the patient information entry section 64 and the light emitting module 21C emits light toward the patient information entry section 64 at an angle of about 45 degrees.

The reader 2 is reciprocally movable directly above the six test instruments B mounted to the mount portion 11. Specifically, the reader is slidably supported by a guide bar (not shown) extending in the direction in which the six test instruments B are arranged and driven by a driving means such as a motor, a pulley or a belt (all not shown). When the reader 2 reciprocates directly above the six test instruments B, the light emitting modules 21A, 21B and the light receiving sensor module 22A read the reagent retaining portions 8A, 8B, 8C and the test item code 63 of the six test instruments B alternately. At the same time, the light emitting module 21C and the light receiving sensor module 22B successively read the patient information entry sections 64 of the six test instruments B. Even when only five or less test instruments B are mounted to the mount portion 11, the reader 2 properly performs the reading operation with respect to the mounted test instruments B. The arrangement of the test item code 63 and the patient information entry section 64 relative to the measurement window 62 may be varied. For instance, the position of the test item code 63 and that of the patient information entry section 64 may be switched. When such a test instrument B is to be used, the light receiving sensor module 22A may read the reagent retaining portions 8A, 8B, 8C and the patient information entry section 64, whereas the light receiving sensor module 22B may read the test item code 63.

For instance, the controller 3 includes a CPU, a ROM, a RAM and an interface. The CPU controls the entirety of the optical measurement apparatus A. The ROM stores various programs or parameters for the processing to be performed by the CPU. The RAM temporarily stores programs or measurement results. The interface performs the inputting and outputting operations of the controller 3. In this embodiment, the controller 3 generates test result output data utilizing the test results obtained by analyzing the image data obtained from the light receiving sensor module 22A, and the image data obtained from the light receiving image sensor module 22B. The test result output data is transmitted to the printer 4.

The printer 4 is a device for outputting the test results of the test instrument B based on the test result output data transmitted from the controller 3. For instance, the printer incorporates a thermal printhead. As shown in FIG. 9, when the test of the test instruments B is completed in the immunochromatography apparatus A, the test results corresponding to the test item are printed.

The external connector 5 is a terminal for transmitting the test result output data to the outside of the optical measurement apparatus A and enables serial communication in conformity to e.g. RS-232C. An information processor such as a personal computer Pc is connected to the external connector 5. The personal computer Pc displays the test result output data transmitted through the external connector 5 on the display or records the test result output data in an internal memory or a recording medium.

The test using the optical measurement apparatus A will be described below using tests for influenza by immunochromatography as an example.

EXAMPLE 1

Figure 8:
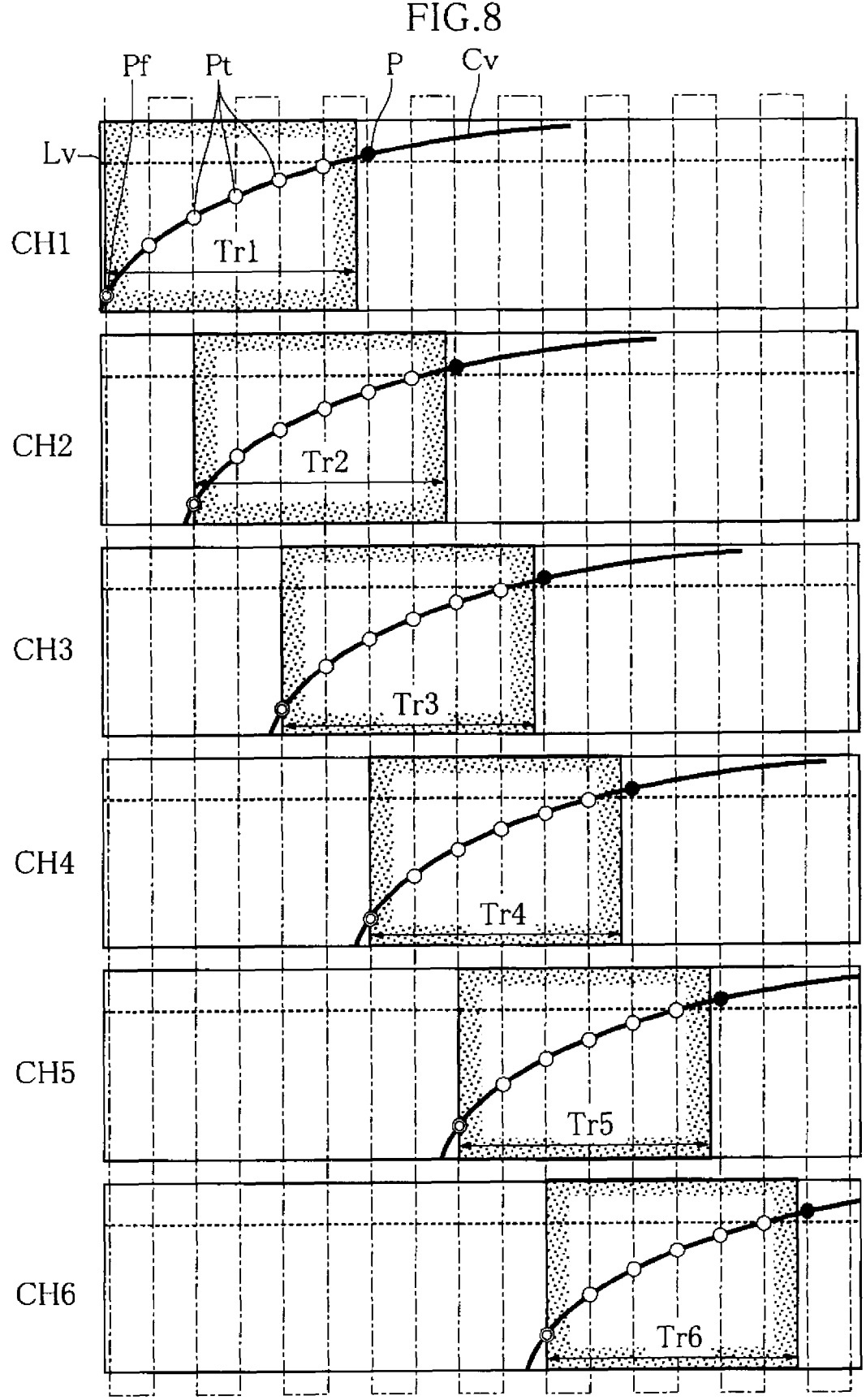
FIG. 8 is a chart showing an example of test using the optical measurement apparatus shown in FIG. 6.

FIG. 8 shows an example of test performed using the optical measurement apparatus A. In this figure, the horizontal axis indicates time, and each of the reaction progress curves Cv indicates the progress of reaction in a relevant one of the test instruments B mounted to the sections CH1-CH6. The reference level Lv represented by the dotted lines in the figure indicates the degree of progress of reaction above which the determination is possible. The single-dashed lines in the figure indicate the route of the reciprocal movement of the reader 2 over the sections CH1-CH6. In this example, tests for influenza are performed with respect to six patients. Specifically, samples taken from six patients are applied to the respective test instruments B, and the test instruments B are successively mounted to the mount portion 11. In each of the six test instruments B, the name of the patient is written in the patient information entry section 64.

First, the test instrument B to which sample is firstly applied is mounted to the section CH1 of the mount portion 11. The sensor 12 detects the mounting of this test instrument and transmits a mount signal to the controller 3. When the reader 2 passes above the test instrument B in the section CH1 for the first time, the reader performs a reading operation Pf to read the test item code 63. In accordance with the test item represented by the test item code 63, the controller 3 sets a reaction completion period Tr1 for the section CH1. After the mounting of the test instrument to the section CH is detected by the sensor 12, the reader 2 performs a reading operation Pt for reading the reagent retaining portions 8A, 8B, 8C a plurality of times, i.e., every time it passes over the section CH1 until the reaction completion period Tr1 lapses. In this reading operations Pt, reading of the reagent retaining portions 8A, 8B, 8C is repeated. In this example, however, the results of the reading operation performed during the reaction completion period Tr1 are not used for the determination. Instead, the result of the reading operation P for reading the reagent retaining portions 8A, 8B, 8C which is performed for the first time after the lapse of the reaction completion period Tr1 is used for the determination of the influenza test. At the time point of the reading operation P, the reaction progress curve Cv is higher than the reference level Lv, because the reaction completion period Tr1 has lapsed after the mounting of the test instrument B to the section CH1.

While the test processing for the section CH1 is performed in the above-described manner, the test processing for the sections CH2-CH6 is also performed. In this example, the test item is the same for all the test instruments B in the sections CH1-CH6, so that reaction completion periods Tr1-Tr6 are the same. Thus, the reading operation is performed successively with respect to the sections CH1-CH6 in the order of mounting. The controller 3 generates test result output data for each of the sections CH1-CH6 based on the test item and test result of each test instrument B and the image data obtained by reading the patient information entry section 64. As shown in FIG. 9, the test result output data is successively printed by the printer 4. The content to be printed includes the date and time, the identification number, the mount section (any of CH1-CH6), the test item, the test result and the name written in the patient information entry section 64. As for the patient's name, the image data of the patient information entry section 64 read by the light receiving sensor module 22B of the reader 2 is printed. To achieve clearer printing, the image data of the patient information entry section 64 may appropriately be subjected to image processing such as binarization by the controller 3.

EXAMPLE 2

Figure 10:
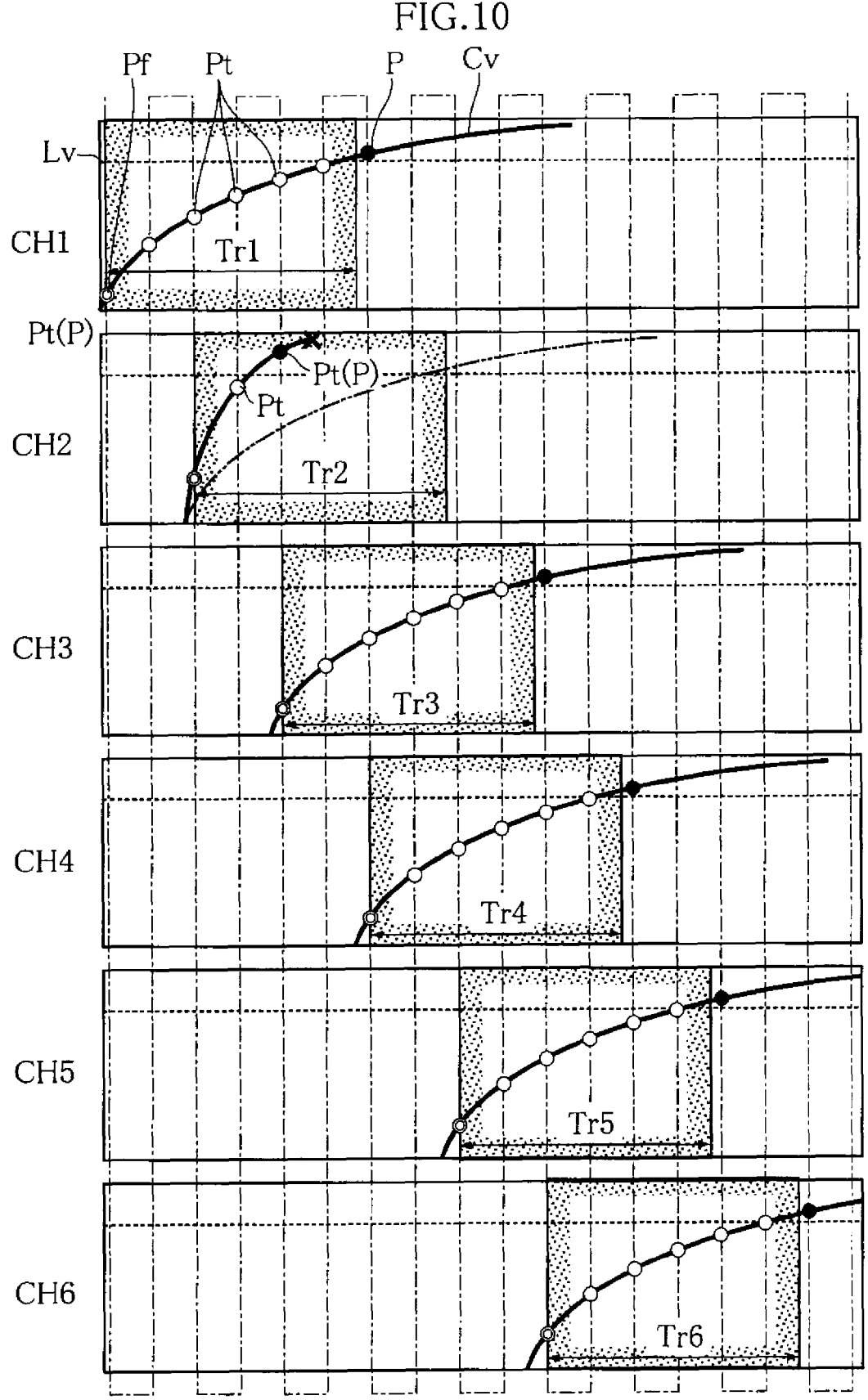
FIG. 10 is a chart showing another example of test using the optical measurement apparatus shown in FIG. 6.
Figure 12:
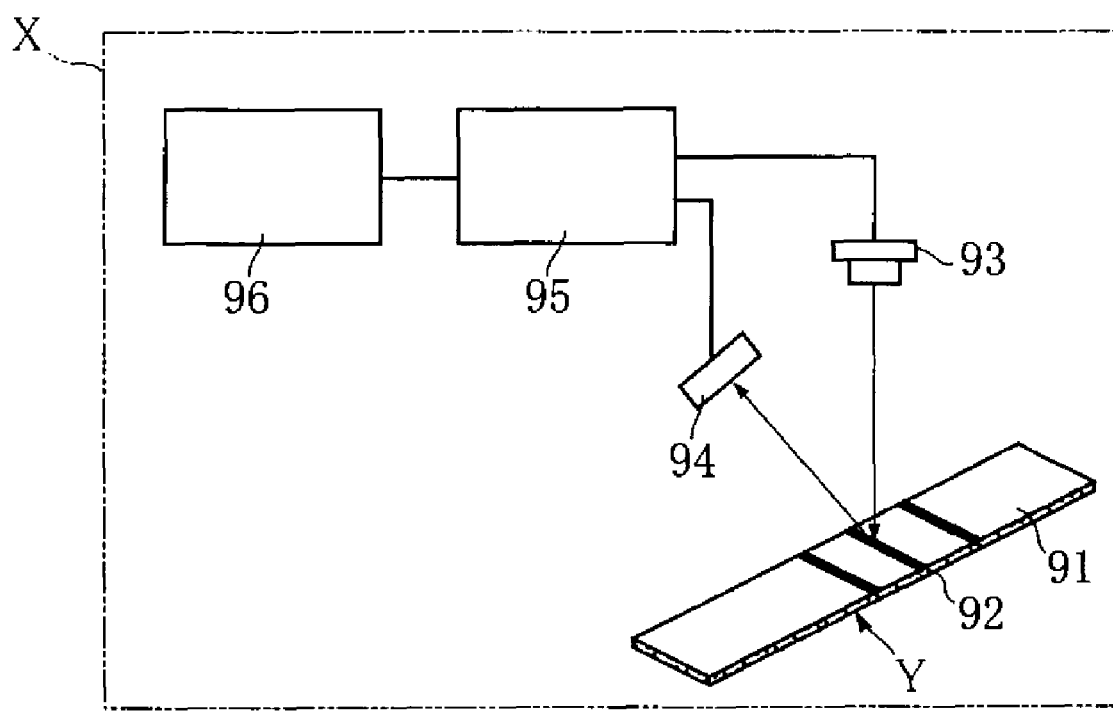
FIG. 12 is a system structure diagram of an example of conventional optical measurement apparatus and test piece.
Figure 13:
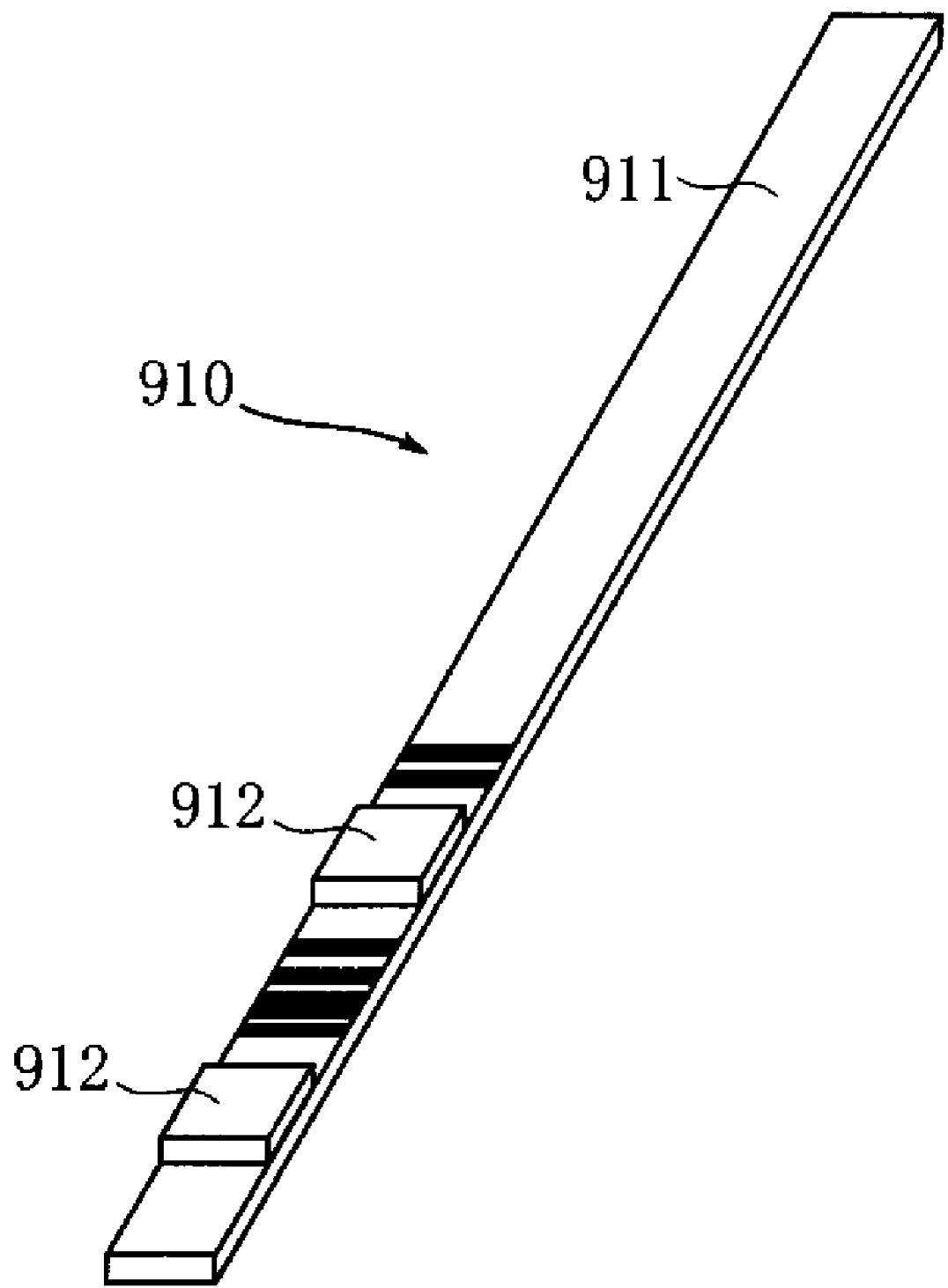
FIG. 13 is a perspective view showing an example of conventional test instrument of a test strip type.
Figure 14:
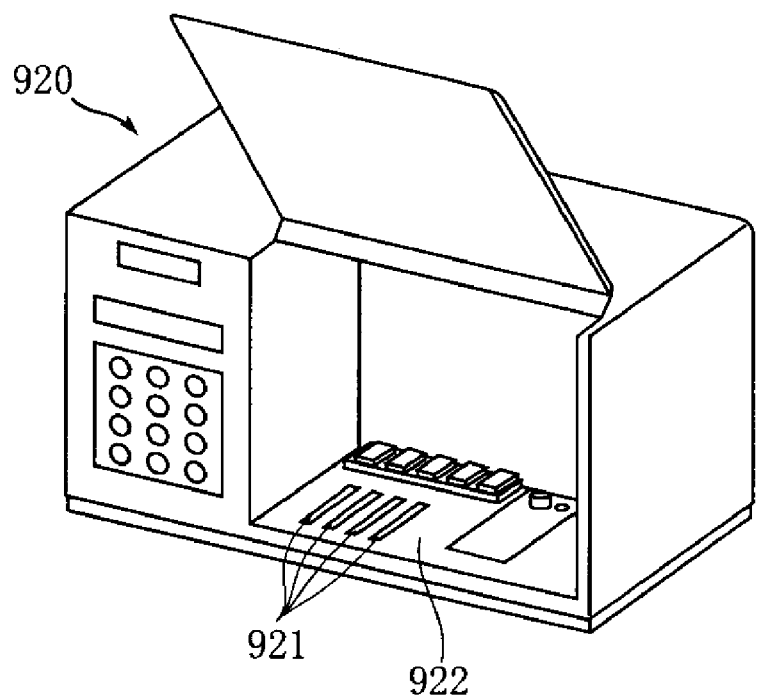
FIG. 14 is a perspective view showing an example of conventional optical measurement apparatus.

FIG. 10 shows still another example of the test performed using the optical measurement apparatus A. In this example, the program executed by the controller 3 is different from that of the above-described example. According to this program, preliminary determination is performed using the result of a reading operation Pt performed before the reaction completion period Tr1-Tr6 lapses after the mounting of the test instrument B.

Specifically, in this example, the preliminary determination is performed with respect to the section CH2 based on the result of the reading operation Pt performed after the reading operation Pf. The reaction progress curve Cv of the section CH2 is steeper than the typical reaction progress curve Cv (indicated by double-dashed lines in the figure). This indicates that the sample applied to the test instrument B in the section CH2 is reacting with the reagent at a higher speed than the normal. Thus, by the preliminary determination based on the result of the second reading operation Pt, it is found that the reference level Lv is already exceeded. Then, the controller 3 determines that the reaction in the test instrument B is completed before the lapse of the reaction completion period Tr2 and causes the printer 4 to perform printing. That is, the second reading operation Pt corresponds to the above-described reading operation P. Thus, the controller 3 finishes the test processing for that test instrument B.

FIG. 11 shows an example of printed test results of this example. In this example, six test instruments are mounted in the order of CH1-CH6. However, since the test processing of the test instrument B mounted to the section CH2 is completed by the above-described preliminary determination, the result of the section CH2 is printed prior to the result of the section CH1.

The advantages of the optical measurement apparatus A and test instrument B will be described below.

According to the embodiment, the printer 4 prints the test result together with the name of the patient. Thus, even when the tests are performed successively with respect to a plurality of patients, the matching of the test result with the patient is easy.

A plurality of test instruments B can be mounted to the optical measurement apparatus A. Once the test instruments B are mounted, the determination is made automatically after the lapse of the reaction completion period Tr1-Tr6 which is determined depending on the test item. Thus, the user of the optical measurement apparatus A does not need to perform time control from the time when the sample is applied to each test instrument B until the time when the determination is possible. This is suitable for such tests as influenza tests which are usually performed for a large number of patients in a short period of time. Since each of the test results accompanies the patient's name, such a situation that the test result of one patient is erroneously determined to be the result of another patient is prevented.

According to the test algorism of Example 2, for the test instrument B in which the reaction of the sample with the reagent progresses faster than the expected speed, the test processing is finished before the lapse of the reaction completion period Tr2. Thus, the time taken for the test processing of the test instrument B is reasonably reduced. When the test of a certain test instrument is completed earlier than normal by the preliminary determination, the printing order of the test results of the plurality of test instruments B may differ from the expected order, i.e., the mounting order of the test instruments B. According to this embodiment, however, the name or the like of the patient written in the patient information entry section 64 is printed with the test result. Thus, even when the test results are printed in an order which is different from the expected order, the matching of each test result with the patient is properly performed. For instance, when an influenza test and an allergy test are to be performed collectively, the reaction completion periods Tr1-Tr6 for the sections CH1-CH6 may differ from each other. In such a case again, the order in which the test is completed, i.e., the printing order may differ from the mounting order. However, since each of the test results is printed together with the name or the like of the patient written in the patient information entry section 64, the matching of each test result with the patient is easily performed.

The patient information entry section 64 of the test instrument B is raised like a platform. Thus, the user or patient is prevented from erroneously writing his or her name at a portion other than the patient information entry section 64. Further, since the patient information entry section 64 has a relatively rough grained surface, writing using e.g. a felt-tip pen is easy.

The test piece and optical measurement apparatus according to the present invention are not limited to the foregoing embodiments. The specific structure of each part of the test piece and optical measurement apparatus according to the present invention may be varied in design in many ways. For instance, the number of the reagent retaining portions 8A, 8B, 8C is not limited to three, and a larger number of reagent retaining portions may be provided.

The patient information entry section 64 is not limited to a rectangular one but may have any shape as long as it enables easy writing of the patient's name or other patient identifying information. Instead of making the surface of the patient information entry section 64 a grained surface, a white paint suitable for absorbing ink may be applied to the surface. Although to raise the patient information entry section 64 is desirable for preventing the writing out of the section, the test piece of the present invention is not limited to this arrangement. For instance, the patient information entry section 64 may be a region defined by a boundary marked on a flat surface.

The reader 2 is not limited to such a structure that the light emitting modules 21A, 21B and the light receiving sensor module 22A perform scanning operation integrally with the light emitting module 21C and the light receiving sensor module 22B. For instance, the light emitting module 21C and the light receiving sensor module 22B for reading the patient information entry section 64 may perform scanning operation independently from the light emitting modules 21A, 21B and the light receiving sensor module 22A. Further, the reader 2 does not necessarily need to include the light emitting module 21C and the light receiving sensor module 22B for exclusively reading the patient information entry section 64, and at least any of the light emitting modules 21A, 21B and the light receiving sensor module 22A may be utilized also for reading the patient information entry section 64. As the output means, either of the printer 4 and the external connector 5 may be selectively provided. The optical measurement apparatus A may include a liquid crystal display for showing the test result output data. The test instrument and optical measurement apparatus of the present invention are not limited to the use for the tests for influenza and may be used for various tests using immunochromatography and various kinds of optical measurement.

The invention claimed is:

1. An optical measurement apparatus to which at least one test instrument is set, comprising:
   the test instrument comprising:
      at least one reagent retaining portion retaining a reagent which reacts with a sample to produce a color reaction; and
      a patient identifying information region for entering patient identifying information, and
   the optical measurement apparatus comprising:
      a reader for reading color development of the reagent retaining portion;
      a controller for performing drive control of the reader and test processing; and
      a printer for data output,
   wherein the reader is configured to read the patient identifying information region,
   wherein the controller generates test result output data using image data of the patient identifying information region obtained by the reading operation or the reader, and
   wherein the printer performs printing based on the test result output data transmitted from the controller, and said printing includes an exact copy of images put in the patient identifying information region.

2. The optical measurement apparatus according to claim 1, further comprising an external connector for data output; wherein the controller is configured to transmit the test result output data through the external connector.

3. The optical measurement apparatus according to claim 1, wherein the optical measurement apparatus is configured to allow setting of a plurality of said test instruments thereto.

* * * * *